United States Patent [19]

Chantler et al.

[11] Patent Number: 4,590,070

[45] Date of Patent: May 20, 1986

[54] CONTRACEPTIVE METHODS

[75] Inventors: Eric N. Chantler, Stockport; Francis G. Hutchinson, Lymm; Deborah A. Sharman, Hadfield, all of United Kingdom

[73] Assignee: Imperial Chemical Industries PLC, London, England

[21] Appl. No.: 638,555

[22] Filed: Aug. 7, 1984

[30] Foreign Application Priority Data

Oct. 14, 1983 [GB] United Kingdom ............... 8327562

[51] Int. Cl.$^4$ .................. A61K 31/74; A61K 31/155
[52] U.S. Cl. ..................................... 424/78; 514/635; 514/843
[58] Field of Search ............... 424/326, 78; 514/635, 514/843

[56] References Cited

FOREIGN PATENT DOCUMENTS 702268 8/1950 United Kingdom .
705838 1/1952 United Kingdom .
1095902 4/1965 United Kingdom .

OTHER PUBLICATIONS

Helgeland et al., Scand. J. Dent. Res., 1971, vol. 79, pp. 209-215.
Searl, Modern Veterinary Practice, 1979, vol. 60, pp. 504-506.
Pineda et al., Theriogenology, 1981, vol. 16, pp. 1-11.
Pineda, Canine Practice, 1978, vol. 5, pp. 34-46.
Pearson et al., The Veterinary Record, 1980, pp. 285-287.
Yu et al., British Journal of Urology, 1976, vol. 48, pp. 371-375.
Halim et al., British Medical Journal, Jul. 14, 1973, p. 110.
The Pharmaceutical Journal, p. 696, (Jun. 1, 1985).
5th International Biorheology Contress Abstracts, vol. 20, No. 4, p. 421, (Aug. 20, 24, 1983).

*Primary Examiner*—Leonard Schenkman
*Attorney, Agent, or Firm*—Cushman, Darby & Cushman

[57] ABSTRACT

This invention relates to the use of polymeric biguanides as topical contraceptive agents, which operate both by rendering vaginal mucus impenetrable to sperm, or by a direct spermicidal action.

3 Claims, No Drawings

CONTRACEPTIVE METHODS

This invention relates to contraceptive methods, and in particular it relates to a method of increasing the viscosity of cervical mucus to such an extent as to render it essentially impermeable to sperm, and to a spermicidal or sperm-immobilising method.

Thus, according to the invention, there is provided a contraceptive method which comprises applying to the mucus in the vagina of a female mammal a mucospissic amount of polymeric biguanide compound which in the form of its free base is a linear polymer in which the recurring unit is represented by the formula:

wherein X and Y stand for bridging groups in which together the total number of carbon atoms directly interposed between the adjacent nitrogen atoms is greater than 9 and less than 17, or an acid-addition salt thereof.

The said bridging groups may consist of polymethylene chains, which optionally may be interrupted, as by oxygen or sulphur atoms, and also they may incorporate cyclic nuclei which themselves may be saturated or unsaturated. The number of carbon atoms directly interposed between the nitrogen atoms when the groups X and/or Y incorporate a cyclic group or groups includes those in that segment of the cyclic group or groups which is the shortest.

The biguanides of the formula I are fully described in United Kingdom Pat. No. 702,268, and are stated to possess good antibacterial activity.

A preferred polymeric biguanide for use in the process of the invention is that wherein X is $-(CH_2)_2-$ to $-(CH_2)_{12}-$, preferably $-(CH_2)_6-$, Y is $-(CH_2)_2-$ to $-(CH_2)_{12}-$, preferably $-(CH_2)_6-$, and which has a number average molecular weight of about 500 to 20,000, and especially preferred is a mixture of polymeric biguanides of the formula:

$$[-(CH_2)_6-NH.C(:NH).NH.C(:NH)NH-]_n \qquad II$$

wherein n varies from about 5 to 10, and having a number average molecular weight of about 1000 to 2200, in the form of their salts with hydrochloric acid.

In this method, the compound of the formula I, when applied to the mucus at a suitable concentration, very rapidly increases its viscosity to the extent that it becomes essentially impenetrable to sperm, and forms a physical barrier to conception in the same way as a rubber sheath or a diaphragm cap.

Besides increasing the viscosity of vaginal mucus, when the mucus comes into contact with a bisbiguanide compound of the formula I, other changes occur in its intrinsic properties, such as its morphology, rheology and water uptake and visco-elastic properties, which can also affect its penetrability to sperm.

In vitro, the compounds of the formula I exert a useful mucospissic effect at concentrations down to about $10^{-7}\%$, and a suitable amount to be applied to the human vagina for contraceptive purposes is from 1 g. to $10^{-7}$ g.

According to a further feature of the invention there is provided a contraceptive method which comprises applying in the vagina of a female mammal a spermicidal or sperm-immobilising amount of a bisbiguanide compound of the formula I as defined above.

Preferred bisbiguanide compounds of the formula I for use in this aspect of the invention are those wherein X and Y are each $-(CH_2)_2-$ to $-(CH_2)_{12}-$, and preferably each is $-(CH_2)_6-$, and which have a number average molecular weight of about 500 to 20,000 and the salts thereof, especially the dihydrochloride, diacetate and digluconate, and especially preferred is a mixture of polymeric biguanides of the formula:

$$[-(CH_2)_6-NH.C(:NH).NH.C(:NH)NH-]_n \qquad II$$

wherein n varies from about 5 to 10, and having a number average molecular weight of about 1000 to 2200, in the form of their salts with hydrochloric acid.

In vitro, the compounds of the formula I exert their spermicidal or sperm-immobilising effect at a minimum concentration of $10^{-7}\%$ w/v.

The compound of the formula I may be applied to mucus in the vagina in conventional manner, for example as a pessary, cream, liquid douche, gel, aerosol foam or impregnated tampon, or in a controlled delivery device of the compound in a polymer matrix.

According to a further feature of the invention there is provided a biguanide compound of the formula I, or a composition thereof, for use as a contraceptive.

The mucospissic and sperm-immobilising properties of the compounds of the formula I are demonstrated in vitro as in the following Examples:

EXAMPLE 1

A mixture of polymeric biguanides of the formula II, wherein n varies from about 5 to 10, and of number average molecular weight from about 1000–2200, in the form of their salts with hydrochloric acid, was dissolved in Tyrodes T6 balanced salt solution containing 4 mg./ml. of human albumin, and then mixed with an equal volume of bovine oestrous mucus. Mixing was achieved by four inversions of the tube containing the mixture, followed by 15 minutes standing to achieve equilibration. A sample of the mixture was then drawn by vacuum into a capillary of rectangular section, 100 μm.×1000 mm×5 cm. One end of the filled capillary was then lowered into a reservoir containing human serum, with a sperm concentration of at least $50 \times 10^6$ per ml. and a motility of at least 80%. The system was incubated for 3 hours at 35° C. in an atmosphere saturated with water vapour, and the distance the leading sperm has then travelled along the capillary was measured by inspection under a microscope at about 200x magnification. The following results were obtained:

| Concentration of biguanide (% w/v) | Mean distance travelled (mm.) | No. of assays |
| --- | --- | --- |
| $10^{-3}$ | 0 | 3 |
| $10^{-4}$ | 0 | 3 |
| $10^{-5}$ | 2.3 | 3 |
| $10^{-6}$ | 11.1 | 3 |
| $10^{-7}$ | 14.1 | 1 |
| 0(control) | 20.5 | 3 |

EXAMPLE 2

The biguanide mixture, as defined in Example 1, (50 μl. of an appropriate aqueous dilution) was dissolved in Tyrodes T6 balanced salt solution supplemented with 4 mg./ml. of human albumin mixed with 50 μl. of fresh human semen with a sperm concentration of at least 50 million per ml. and a motility of at least 80%, and incubated at 25° C. for 3 minutes. The motility of the sperm so treated was measured by one of two methods:

(a) If the concentration of biguanide caused protein precipitation, motility was estimated by phase contrast microscopy at 200x magnification in a 10 μm. deep counting chamber.

(b) If the solution remained optically clear, motility was measured by laser Doppler spectroscopy. This technique involves the analysis by auto-correlation of the fraction of the scattered laser light which contains the Doppler-shifted frequencies generated by interaction between the incident laser and the sperm head.

The following results were obtained:

| Concentration of biguanide (% w/v) | Mean % inhibition of motility | No. of assays |
|---|---|---|
| 10.0 | 100 | 4 |
| 1.0 | 100 | 4 |
| 0.1 | 67.6 | 4 |
| 0.01 | 57.5 | 4 |
| 0.001 | 41.4 | 4 |
| 0.0001 | 21.0 | 1 |

What we claim is:

1. A contraceptive method which comprises applying to the mucus in the vagina of a female mammal a mucospissic, spermicidal or sperm-immobilizing amount of polymeric biguanide compound which in the form of its free base is a linear polymer in which the recurring unit is represented by the formula:

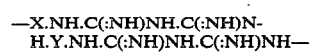

wherein X and Y stand for bridging groups in which together the total number of carbon atoms directly interposed between the adjacent nitrogen atoms is greater than 9 and less than 17, or an acid-addition salt thereof.

2. A method as claimed in claim 1 wherein, in the polymeric biguanide, X is $-(CH_2)_2-$ to $-(CH_2)_{12}-$ and Y is $-(CH_2)_2-$ to $-(CH_2)_{12}-$, and the polymeric biguanide has a number average molecular weight of 500 to 20,000.

3. A method as claimed in claim 2 wherein the polymeric biguanide has the formula:

wherein n varies from 5 to 10, and a number average molecular weight of 1000 to 2200.